United States Patent
Thakur et al.

(10) Patent No.: US 11,802,466 B2
(45) Date of Patent: Oct. 31, 2023

(54) OPTIMIZATION TECHNIQUE FOR CO2-EOR MISCIBILITY MANAGEMENT IN AN OIL RESERVOIR

(71) Applicant: University of Houston System, Houston, TX (US)

(72) Inventors: Ganesh C. Thakur, Houston, TX (US); Peila Chen, Houston, TX (US); Sriram Balasubramanian, Houston, TX (US); Sushanta Bose, Katy, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 433 days.

(21) Appl. No.: 17/281,645

(22) PCT Filed: Oct. 1, 2019

(86) PCT No.: PCT/US2019/054100
§ 371 (c)(1),
(2) Date: Mar. 31, 2021

(87) PCT Pub. No.: WO2020/072514
PCT Pub. Date: Apr. 9, 2020

(65) Prior Publication Data
US 2021/0372246 A1 Dec. 2, 2021

Related U.S. Application Data

(60) Provisional application No. 62/740,379, filed on Oct. 2, 2018.

(51) Int. Cl.
*E21B 43/16* (2006.01)
*E21B 49/08* (2006.01)
(Continued)

(52) U.S. Cl.
CPC ............ *E21B 43/164* (2013.01); *E21B 47/06* (2013.01); *E21B 49/0875* (2020.05); *G01N 7/14* (2013.01);
(Continued)

(58) Field of Classification Search
CPC ...... E21B 43/16; E21B 43/164; E21B 43/166; E21B 43/168
See application file for complete search history.

(56) References Cited

U.S. PATENT DOCUMENTS 3,620,304 A * 11/1971 Hearn ................... E21B 43/168
166/402
3,995,693 A * 12/1976 Cornelius ............. E21B 43/164
166/402
(Continued)

FOREIGN PATENT DOCUMENTS

CA          3000260 C  * 12/2018  ........... E21B 43/164
CN        102337874 A     2/2012
(Continued)

OTHER PUBLICATIONS

Translation of CN-108266165-A (Year: 2018).*
(Continued)

*Primary Examiner* — Angela M DiTrani Leff
(74) *Attorney, Agent, or Firm* — CONLEY ROSE, P.C.

(57) ABSTRACT

A method of recovering crude oil from a reservoir by: determining a depletion pressure for providing a lights-depleted crude oil comprising a reduced amount of light ends including methane, nitrogen, carbon dioxide ($CO_2$), or a combination thereof and having a $CO_2$ multi contact Minimum Miscibility Pressure ($CO_2$-MMP) below a $CO_2$-MMP of a native crude oil, wherein the native crude oil is crude oil extracted from the reservoir prior to primary oil recovery therefrom; depleting the pressure of the reservoir
(Continued)

from an initial reservoir pressure to the determined depletion pressure, thus providing the lights-depleted crude oil; repressurizing the reservoir to an operating pressure for recovering the lights-depleted crude oil from the reservoir via carbon dioxide ($CO_2$) injection; injecting $CO_2$ into the reservoir via at least one injection well; and recovering at least a portion of the lights-depleted crude oil from the reservoir via at least one production well.

23 Claims, 5 Drawing Sheets

(51) Int. Cl.
*E21B 47/06* (2012.01)
*G01N 7/14* (2006.01)
*G01N 33/28* (2006.01)

(52) U.S. Cl.
CPC ......... *G01N 33/28* (2013.01); *G01N 33/2823* (2013.01)

(56) References Cited

U.S. PATENT DOCUMENTS

| | | | | |
|---|---|---|---|---|
| 4,187,910 | A * | 2/1980 | Cornelius | E21B 43/164 166/305.1 |
| 4,224,992 | A * | 9/1980 | Comberiati | E21B 43/164 166/402 |
| 4,455,860 | A * | 6/1984 | Cullick | G01N 33/2823 73/19.11 |
| 4,513,821 | A * | 4/1985 | Shu | E21B 36/001 166/402 |
| 4,736,793 | A * | 4/1988 | Djabbarah | E21B 43/164 166/402 |
| 4,766,558 | A * | 8/1988 | Luks | E21B 43/16 700/265 |
| 5,046,561 | A * | 9/1991 | Huang | E21B 43/164 166/402 |
| 5,074,357 | A * | 12/1991 | Haines | E21B 43/168 166/267 |
| 5,505,074 | A * | 4/1996 | Mihcakan | G01N 33/2823 73/19.01 |
| 7,707,013 | B2 | 4/2010 | Valdez et al. | |
| 2014/0000884 | A1 | 1/2014 | Milam et al. | |
| 2016/0047226 | A1* | 2/2016 | Hawthorne | G01N 33/2823 166/305.1 |
| 2020/0202060 | A1* | 6/2020 | Thakur | E21B 43/16 |

FOREIGN PATENT DOCUMENTS

| | | | | |
|---|---|---|---|---|
| CN | | 108266165 A | * | 7/2018 |
| WO | WO-2016057780 A1 | * | 4/2016 | E21B 28/00 |

OTHER PUBLICATIONS

PCT/US2019/054100 International Search Report and Written Opinion dated Jan. 2, 2020 (9 p.).

Bon, Johannes, Laboratory and Modelling Studies on the Effects of Injection Gas Composition on CO2-Rich Flooding in Cooper Basin, Doctorate Thesis, The University of Adelaide, Feb. 2009 (227 p.).

* cited by examiner

OPTIMIZATION TECHNIQUE FOR CO2-EOR MISCIBILITY MANAGEMENT IN AN OIL RESERVOIR

CROSS-REFERENCE TO RELATED APPLICATIONS

This application is a 35 U.S.C. § 371 national stage application of PCT/US2019/054100 filed Oct. 1, 2019, and entitled "Optimization Technique for CO2-EOR Miscibility Management in an Oil Reservoir," which claims priority to U.S. Provisional Patent Application No. 62/740,379 filed Oct. 2, 2018, and entitled, "Optimization Technique for CO2-EOR Miscibility Management in an Oil Reservoir", the disclosure of which is hereby incorporated herein for purposes not contrary to this disclosure.

TECHNICAL FIELD

The present disclosure relates to a method of recovery of light crude oil from an oil reservoir; still more particularly, this disclosure relates to recovering light crude oil from an oil reservoir at a reservoir pressure (also referred to herein as an 'operating pressure') that is less than the multi contact Minimum Miscibility Pressure (MMP) of carbon dioxide ($CO_2$) for a native oil in the reservoir; still more particularly, the present disclosure provides a method of recovering crude oil from an oil reservoir via optimization of $CO_2$ miscibility during tertiary oil recovery.

BACKGROUND

There are three stages of oil recovery from a reservoir formation: primary, secondary and tertiary. Primary recovery is the first stage in developing an oil and gas reservoir. During this stage, reservoir energy is utilized, and reservoir pressure is depleted as oil and gas are produced. However, primary recovery leaves a lot of oil behind in the reservoir. With the exception of water influx and gravity drainage reservoirs, where recovery factors are much higher, primary recovery typically varies between 5% and 30% of initial oil in place. Secondary and/or tertiary recovery methods are utilized to provide enhanced oil recovery (EOR). Secondary recovery methods are usually applied after reservoir energy has been depleted and oil can no longer be produced economically through primary recovery. Secondary recovery methods include waterflooding, during which water is injected into the reservoir to drive the oil left behind to producer wells. Tertiary recovery follows secondary recovery methods and can include injection of gases or chemicals to obtain further oil recovery after waterflooding.

Miscible gas injection is a tertiary recovery technique which is accomplished by injecting, into a reservoir, a gas that is miscible with the oil in the reservoir and thus can effectively displace oil from the pores to producers (e.g., producing wells). Miscible displacement is more effective than immiscible displacement in recovering the oil trapped from the pores of the rock, because the two-phase boundary between oil and the gas gets eliminated when miscibility is achieved. Consequently, the Interfacial Tension (IFT) between the two fluids reduces to near zero when miscibility is achieved, leading to elimination of capillary trapping forces. As a result, the recovery efficiency of oil is maximized during the miscible displacement process.

Carbon dioxide ($CO_2$) has widely been utilized for miscible gas injection in a variety of reservoirs. Miscibility of $CO_2$ with oil results in reduction in oil viscosity and causes oil swelling. Both of these effects lead to enhanced oil recovery from the formation. To achieve miscibility between $CO_2$ and crude oil, reservoir pressure has to be higher than a threshold value; this threshold pressure is called multiple contact Minimum Miscibility Pressure (MMP). For a given crude oil, MMP can be determined through laboratory Pressure Volume Temperature (PVT) experiments conducted at reservoir temperature for a crude oil composition existing in the reservoir. These include the slim tube method and the rising bubble method.

When reservoir pressure is higher than the MMP, carbon dioxide extracts crude oil components by vaporizing gas drive. During this mechanism, lighter components (mostly C1) of the crude oil are extracted into the $CO_2$ vapor phase. As a result, the vapor phase becomes progressively enriched with crude oil components. This continues until the vapor phase is miscible with oil in all proportions.

Conventionally, before commencing $CO_2$ injection into a reservoir, the reservoir is pressurized by performing water injection so that the reservoir pressure rises above the multi contact MMP of $CO_2$ in the crude oil (also referred to herein as the '$CO_2$-crude oil MMP' or simply the '$CO_2$-MMP' or 'MMP') of the original reservoir oil. However, for certain reservoirs, the bubble point pressure of the crude oil is higher than the $CO_2$-MMP. In such cases, bubble point pressure is considered as $CO_2$-MMP and the reservoir is typically then pressurized to the bubble point pressure prior to $CO_2$ injection into the reservoir. This presents a problem where bubble point pressure and $CO_2$-MMP are both high (e.g., 3000-4000 psi). To increase the pressure to this level, significant water typically has to be injected before a $CO_2$ flood is commenced. This process becomes very demanding operationally. The problem can be mitigated if the $CO_2$-MMP of the crude oil can be lowered; however, few methods have heretofore been proposed to lower the $CO_2$-crude oil MMP. Accurate determination and management of the multi contact MMP of $CO_2$ in the crude oil is thus important for designing a viable $CO_2$ flood process for oil reservoirs.

Accordingly, a need exists for enhanced methods of miscibility management during EOR and methods of recovering oil from a reservoir therewith.

SUMMARY

Herein disclosed is a method of recovering crude oil from a reservoir, the method comprising: determining a depletion pressure for providing a lights-depleted crude oil comprising a reduced amount of light ends including methane, nitrogen, carbon dioxide ($CO_2$), or a combination thereof and having a $CO_2$ multi contact Minimum Miscibility Pressure ($CO_2$-MMP) below a $CO_2$-MMP of a native crude oil, wherein the native crude oil is crude oil extracted from the reservoir prior to primary oil recovery therefrom; depleting the pressure of the reservoir from an initial reservoir pressure to the determined depletion pressure, thus providing the lights-depleted crude oil; repressurizing the reservoir to an operating pressure for recovering the lights-depleted crude oil from the reservoir via carbon dioxide ($CO_2$) injection; injecting $CO_2$ into the reservoir via at least one injection well; and recovering at least a portion of the lights-depleted crude oil from the reservoir via at least one production well.

Also disclosed herein is a method of recovering crude oil from a reservoir via carbon dioxide ($CO_2$) injection, the method comprising: determining a depletion pressure by: (i) determining a $CO_2$ multi contact Minimum Miscibility Pressure ($CO_2$-MMP) for a sample having a composition of a native crude oil, wherein the native crude oil is crude oil extracted from the reservoir prior to primary oil recovery therefrom; (ii) pressure depleting a sample having a composition of the native crude oil to a test pressure; (iii) removing excess gas from the pressure depleted sample to provide a lights-depleted crude oil sample; (iv) measuring the $CO_2$-MMP for the lights-depleted crude oil sample at the test pressure; (v) repeating (ii) through (iv) for a plurality of test pressures; and (vi) determining the depletion pressure as the test pressure at which a lowest $CO_2$-MMP is obtained, depleting a pressure in the reservoir from an initial reservoir pressure to a pressure greater than or equal to the depletion pressure, whereby light components are removed from the reservoir to provide a lights-depleted crude oil in the reservoir, wherein light components comprise methane ($CH_4$), nitrogen ($N_2$), $CO_2$, or a combination thereof; and producing at least a portion of the lights-depleted crude oil from the reservoir via $CO_2$ injection at a reservoir pressure (e.g., an 'operating pressure') of greater than or equal to the $CO_2$-MMP of the lights-depleted crude oil.

Further described herein is a method of recovering crude oil from a reservoir via carbon dioxide ($CO_2$) injection, the method comprising: injecting $CO_2$ into the reservoir at a reservoir pressure (e.g., or 'operating pressure') of less than a $CO_2$ multi contact Minimum Miscibility Pressure ($CO_2$-MMP) of a native crude oil, wherein the native crude oil is crude oil extracted from the reservoir prior to primary oil recovery therefrom.

Also disclosed herein is a method of recovering crude oil from a reservoir via carbon dioxide ($CO_2$) injection, the method comprising: depleting a pressure in the reservoir from an initial reservoir pressure, whereby light components are removed from the reservoir to provide a lights-depleted crude oil in the reservoir, wherein light components comprise methane ($CH_4$), nitrogen ($N_2$), $CO_2$, or a combination thereof; and producing at least a portion of the lights-depleted crude oil from the reservoir via $CO_2$ injection at a reservoir pressure (or 'operating pressure') of greater than or equal to the $CO_2$-MMP of the lights-depleted crude oil and less than the $CO_2$-MMP of a native crude oil, wherein the native crude oil is crude oil extracted from the reservoir prior to primary recovery therefrom.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the detailed description hereinbelow is to be regarded as illustrative in nature and not restrictive.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

It should be understood at the outset that although an illustrative implementation of one or more exemplary embodiments are provided below, the disclosed compositions, methods, and/or products may be implemented using any number of techniques, whether currently known or in existence. The disclosure should in no way be limited to the illustrative implementations, drawings, and techniques illustrated hereinbelow, including the exemplary designs and implementations illustrated and described herein, but may be modified within the scope of the appended claims along with their full scope of equivalents.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ."

As utilized herein, the bubble point pressure is the pressure at some reference temperature that the first bubble of gas is liberated from the liquid phase, and is also known as the saturation pressure. The reference temperature can be the reservoir temperature.

As utilized herein, the multi contact Minimum Miscibility Pressure (MMP) is the lowest pressure for which a gas can develop miscibility through a multi contact process with a given reservoir oil at the reservoir temperature. The reservoir to which the process can be applied can be operated at or above the MMP to develop multi contact MMP.

OVERVIEW

The present disclosure provides a method for optimizing the MMP of a $CO_2$-crude oil mixture in a reservoir so that $CO_2$ can be utilized more effectively in a miscible displacement process. As described herein, the reservoir can be optimally depleted such that the lighter ends (e.g., C1, C2) are liberated from the crude oil and get produced at the producers (e.g., producing wells). The depletion strategy proposed here may be especially useful if the reservoir in question has an initial bubble point pressure that is similar in magnitude to or even higher than the $CO_2$-MMP. Repressurization of such a reservoir to bring the reservoir to bubble point pressure, as conventionally performed, would require significant injection of a fluid, such as water, which can be very operationally demanding. Furthermore, most of the light ends, such as methane ($CH_4$), have already escaped to the producer wells. The resultant oil is now depleted of the light ends and enriched with intermediate ends.

Thus, a method of tertiary oil recovery via $CO_2$ injection according to this disclosure comprises, prior to performing a $CO_2$ flood, optimally depleting the reservoir so that the light ends (C1) are liberated. The depleted reservoir oil will now be enriched with intermediates. This depleted oil will have a lower bubble point pressure and a lower $CO_2$-MMP than the original oil. A carbon dioxide flood for such a lights-depleted reservoir will not require the pressure to be restored to original reservoir $CO_2$-MMP prior to $CO_2$ injection, and will thus be less operationally demanding.

Figure 1:
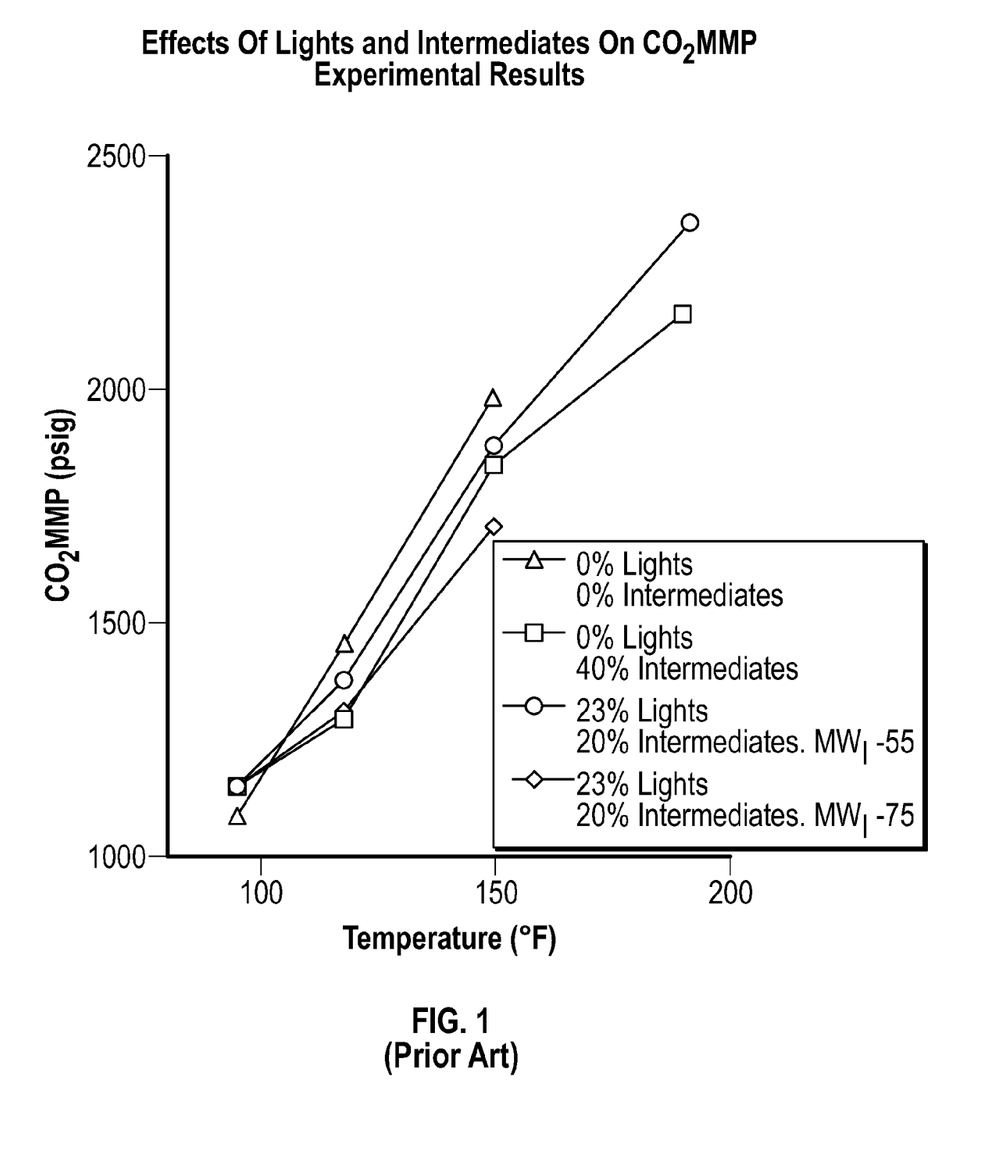
FIG. 1 is a plot of $CO_2$-MMP as a function of temperature (° F.) for crude oils having varying composition of light components and intermediate components.

In general, the presence of a higher concentration of light components (for example, methane ($CH_4$)) in a crude oil increases the MMP. This effect was observed by Yellig and Metcalfe (1980) who performed experiments to analyze the effect of light and intermediate components in oil on the $CO_2$-MMP, the experimental results of which are presented in FIG. 1. In this study, oil consisting of three fractions was considered: (1) a light fraction comprising predominantly C1 (i.e., methane) and small amounts of nitrogen ($N_2$) and $CO_2$; (2) an intermediate fraction comprising hydrocarbons having molecular weights (MWs) between those of C2 and C6 (e.g., between the MWs of ethane and hexane); and (3) a heavy fraction with components having a molecular weight greater than normal C7 (n-heptane). The average MW of the C7+ fractions was kept constant at 201 g/mole; an average MW of the C2-C6 components was 55 g/mole for three experiments and 75 g/mole for one experiment. The curve in FIG. 1 shows that the measured $CO_2$-MMP was lower for crude oils having a higher amount (e.g., mole fraction) of intermediates. Moreover, the $CO_2$-MMP was observed to be lower when crude oil with a higher MW intermediate fraction was used than when a crude oil with a lower MW intermediate fraction was used. The curve also shows the variation of $CO_2$-MMP with temperature; the $CO_2$-MMP was higher at higher temperatures for each composition.

Method of Recovering Crude Oil Via $CO_2$ Injection

According to embodiments, herein disclosed is a method of recovering crude oil from a reservoir via $CO_2$ injection. Such a method of recovering crude oil will now be described with reference to FIG. 2, which is a schematic flow diagram of a method I of recovering crude oil from a reservoir. Crude oil recovery method I comprises determining a depletion pressure at 10, depleting the reservoir to the depletion pressure at 20, injecting $CO_2$ into the reservoir at a reservoir pressure (or 'operating pressure') below the $CO_2$-MMP for the native crude oil at 30, and producing crude oil from the reservoir at 40. The method can further comprise repressurizing the reservoir to an operating pressure (e.g., a pressure greater than or equal to the depletion pressure) for producing the crude oil from the reservoir via carbon dioxide ($CO_2$) injection at 25.

Determining Depletion Pressure 10

Figure 2:
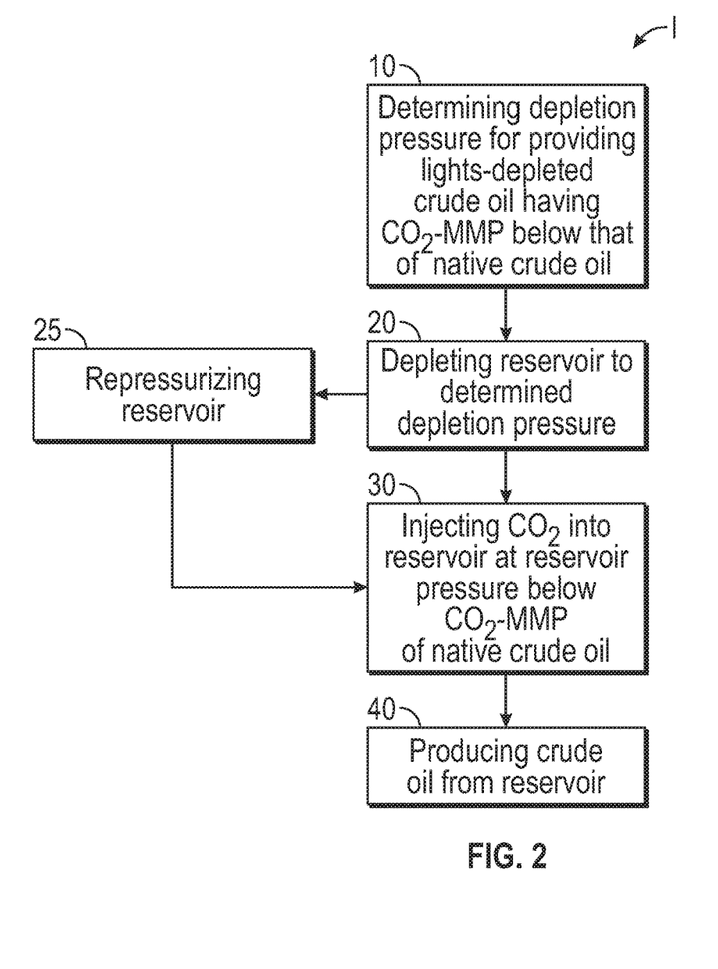
FIG. 2 is a schematic flow diagram of a method of recovering crude oil from a reservoir, according to embodiments of this disclosure.

As noted above, a method of recovering crude oil from a reservoir via $CO_2$ injection according to this disclosure comprises determining a depletion pressure at 10. The depletion pressure is a pressure to which the reservoir can be reduced to provide, in the pressure reduced or 'depleted' reservoir, a lights-depleted crude oil having a $CO_2$-MMP below that of a native crude oil. As utilized herein, 'native' refers to a condition of the reservoir prior to production of any oil from the reservoir through pressure depletion (i.e., prior to primary recovery).

The depletion pressure may be selected as the pressure that provides for a lights-reduced crude oil having a minimum $CO_2$-MMP. By depleting the reservoir to the depletion pressure, the original or 'native' crude oil is depleted so that light ends (mostly C1) are liberated and produced at one or more producer wells. The crude oil remaining in the reservoir then has a lower bubble point pressure and a lower MMP owing to its lower concentration of light ends and higher concentration of intermediate components.

Determining the depletion pressure can comprise determining as the depletion pressure that pressure which provides for optimal depletion of light ends from the reservoir. The optimal depletion may be provided by a depletion pressure that is high enough to keep the intermediates in the solution in the reservoir so that a concentration thereof in the crude oil increases. Such an optimized depletion of light ends from the reservoir at the depletion pressure can, in embodiments, simultaneously lower the MMP and the bubble point pressure of the crude oil so that an injection pressure (also referred to herein as an operating pressure) utilized for the $CO_2$ flood can be lower than conventionally employed.

In embodiments, the depletion pressure is a pressure below which the $CO_2$-MMP does not further decrease, which pressure can be determined via laboratory $CO_2$-MMP experiments on the native crude oil.

Figure 3:
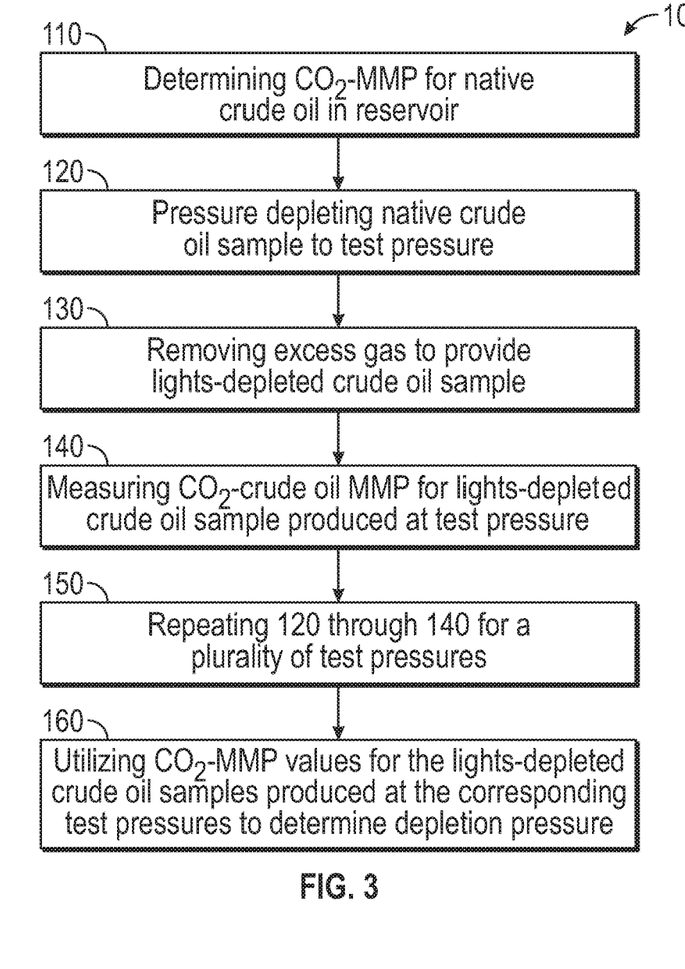
FIG. 3 is a schematic flow diagram of a method of determining a depletion pressure to which a reservoir can be depleted prior to injecting $CO_2$ during tertiary enhanced oil recovery, according to embodiments of this disclosure.

FIG. 3 is a schematic flow diagram of a method 10' of determining a depletion pressure (e.g., an optimum depletion pressure) to which a reservoir can be depleted prior to injecting $CO_2$ during tertiary enhanced oil recovery, according to embodiments of this disclosure. The method 10' can be performed in a laboratory, for example. In the embodiment of FIG. 3, method 10' of determining the depletion pressure (e.g., the optimum depletion pressure) comprises determining the $CO_2$-MMP for a sample having a composition of the native crude oil at 110; pressure depleting a sample having a composition of the native crude oil to a test pressure at 120; removing excess gas to provide a lights-depleted crude oil sample at 130; measuring the $CO_2$-MMP for the lights-depleted crude oil sample produced at the test pressure at 140; repeating steps 120 through 140 for a plurality of test pressures at 150; and utilizing the $CO_2$-MMP values for the lights-depleted crude oil samples at the corresponding test pressures to determine the depletion pressure at 160.

In embodiments, utilizing the $CO_2$-MMP values for the lights-depleted crude oil samples at the corresponding test pressures to determine the depletion pressure to which the reservoir is reduced to provide a lights-depleted crude oil at 160 comprises determining the depletion pressure as the test pressure at which the $CO_2$-MMP for a lights-depleted crude oil sample is a minimum. That is, when the crude oil starts to lose intermediates, the $CO_2$-MMP may not decrease any further. In embodiments, the $CO_2$-MMP as a function of the test pressure for each of the samples is examined (e.g., plotted on a graph), and the depletion pressure is determined as the test pressure at which the $CO_2$-MMP for the lights-depleted crude oil sample is a minimum (e.g., the minimum $CO_2$-MMP is selected from the plot). In embodiments, a curve of $CO_2$-crude oil MMP with test pressure is produced and utilized to determine the depletion pressure (e.g., the optimum depletion pressure) to which the reservoir can be depleted prior to $CO_2$ injection.

Depleting Reservoir to the Determined Depletion Pressure at 20

As noted above, a method of recovering crude oil from a reservoir via $CO_2$ injection according to this disclosure comprises pressure depleting the reservoir (i.e., reducing the pressure of the reservoir and/or allowing it to reduce) to the determined depletion pressure (which can be an optimized depletion pressure which provides a minimum $CO_2$-MMP in the resulting lights-depleted crude oil) at 20. Depleting the pressure of the reservoir from an initial reservoir pressure to the determined depletion pressure provides the lights-depleted crude oil in the reservoir, via production of released light ends. Reducing the pressure of the reservoir to the depletion pressure can be performed by any means known to those of skill in the art, in embodiments.

In embodiments, the lights-depleted crude oil provided by reducing the reservoir pressure to the depletion pressure comprises a mole fraction of light hydrocarbons that is at least 10%-30% less than a mole fraction of light components in the native crude oil, wherein the light components comprise methane ($CH_4$), nitrogen ($N_2$), $CO_2$, or a combination thereof.

In embodiments, the lights-depleted crude oil comprises a mole fraction of intermediate components that is at least 10-30% greater than a mole fraction of intermediate hydrocarbons in the native crude oil, wherein the intermediate components have molecular weights (MWs) between that of ethane (C2) and hexane (C6).

In embodiments, the $CO_2$-MMP for the lights-depleted crude oil obtained via pressure depletion at 20 is at least 15-35% less than the $CO_2$-MMP for the native crude oil.

In embodiments, a bubble point pressure of the lights-depleted crude oil obtained via pressure depletion at 20 is at least 25-45% less than the bubble point pressure of the native crude oil, wherein the bubble point pressure is the pressure at which a first bubble of gas is liberated from the liquid phase at the reservoir temperature.

Injecting $CO_2$ into Reservoir at a Pressure Below Native $CO_2$-MMP at 30

As noted above, a method of recovering crude oil from a reservoir via $CO_2$ injection according to this disclosure comprises injecting $CO_2$ into the reservoir at a reservoir pressure (also referred to herein as an 'operating pressure') below the $CO_2$-MMP of the native crude oil at 30. In embodiments, the operating pressure is at least 15-35% less than the $CO_2$-MMP for the native crude oil. In embodiments, the operating pressure is below the bubble point pressure of the native crude oil, wherein the bubble point pressure is the pressure at which a first bubble of gas is liberated from the liquid phase at the reservoir temperature. In embodiments, the operating pressure is at least 1-5% less than the bubble point pressure of the native crude oil.

Repressurizing Reservoir at 25

The operating pressure for $CO_2$ injection can be greater than or equal to the depletion pressure, in embodiments. In embodiments, as noted above, a method of recovering crude oil from a reservoir via $CO_2$ injection according to this disclosure can further comprise repressurizing the reservoir to a $CO_2$ injection pressure (also referred to herein as an operating pressure) at 25, prior to injecting $CO_2$ into the reservoir at 30. In embodiments, the reservoir is repressurized to a pressure (e.g., an operating pressure) above the depletion pressure at 25. In embodiments, the operating pressure is in a range of from about 0 to about 500 psi, from about 50 to about 500 psi, from about 100 to about 200 psi, or about 100, 200, or 300 psi greater than the depletion pressure.

Producing Lights-Depleted Crude Oil from Reservoir at 40

Figure 4:
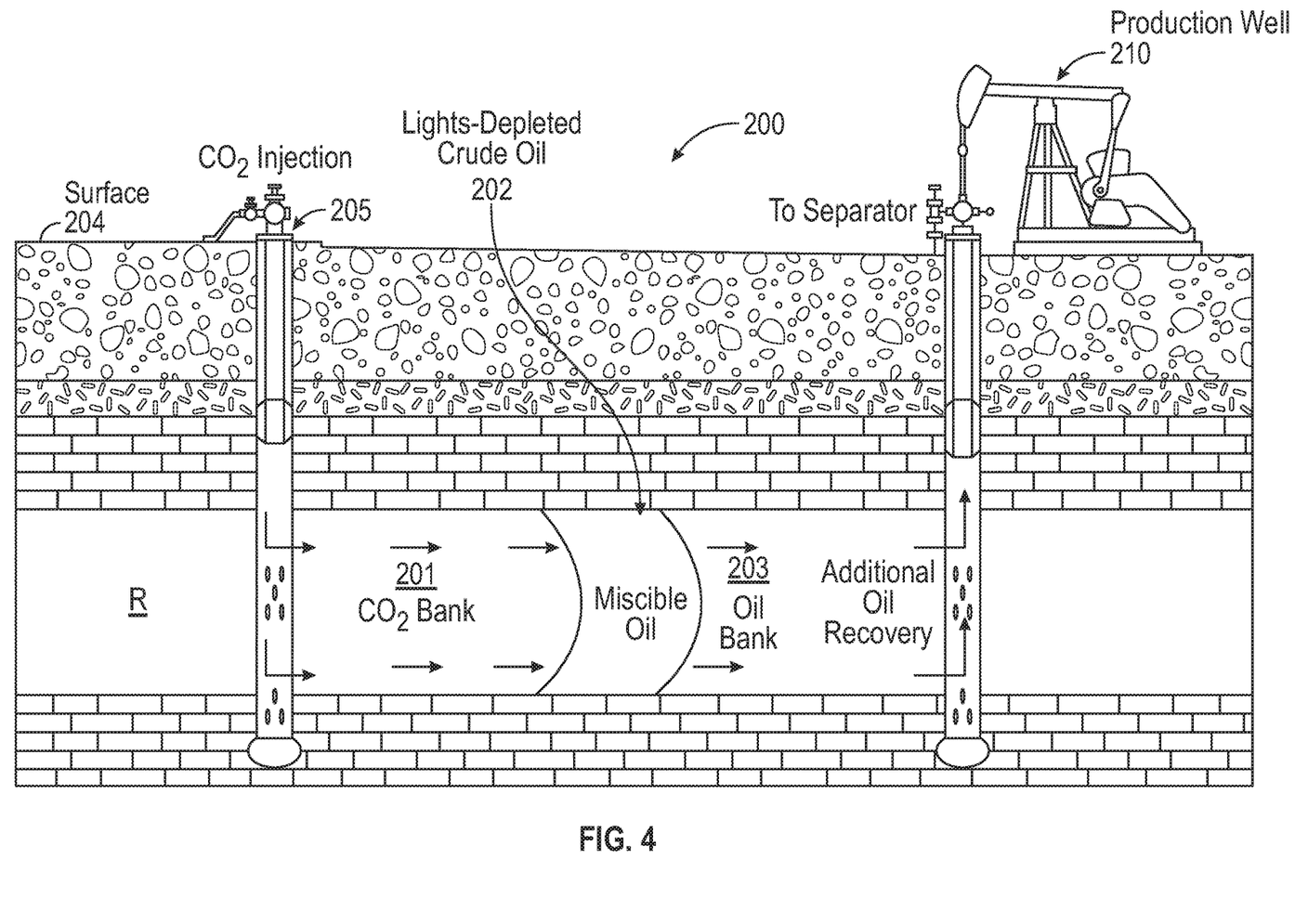
FIG. 4 is a schematic of a miscible $CO_2$-flood, according to an embodiment of this disclosure.

As noted above, a method of recovering crude oil from a reservoir via $CO_2$ injection according to this disclosure comprises producing crude oil from the reservoir at 40. FIG. 4 is a schematic of a miscible $CO_2$-flood 200 for crude oil depleted of light ends (e.g., $CH_4$), according to an embodiment of this disclosure. As depicted in the embodiment of FIG. 4, a $CO_2$ flood can be injected into a reservoir R comprising the lights-reduced crude oil via at least one injection well 205, and crude oil (e.g., at least a portion of the lights-reduced crude oil) can be produced from the reservoir R via at least one production well 210. The at least one injection well and the at least one production well maybe in fluid communication, as depicted in FIG. 4. Injection of the $CO_2$ into injection well 205 at step 30 (of FIG. 2) provides a $CO_2$ bank or flood 201 that pushes an oil bank 203 to production well 210, whereby oil is recovered at the surface 204. Due to depletion of the light ends (e.g., $CH_4$) provided by depleting the reservoir R to the determined depletion pressure at step 20 (of FIG. 2), the lights-depleted crude oil 202 is miscible with the $CO_2$ bank 201, and enhanced oil recovery is obtained. The produced oil may be sent to a separator for separating water and gas from the produced oil.

Features and Potential Advantages

This disclosure provides a novel method of managing $CO_2$-crude oil MMP in a reservoir by depleting light ends therefrom via pressure reduction/depletion. Conventionally, the reservoir pressure is elevated to the $CO_2$-MMP of the original/native crude oil prior to $CO_2$ injection. Moreover, if the bubble point pressure of the original crude oil is higher than the $CO_2$-MMP, the pressure is traditionally elevated to the bubble point pressure. This disclosure provides a novel way to approach this problem, whereby crude oil recovery via $CO_2$-injection can be effected at lower than conventional pressures (e.g., at pressures lower than the $CO_2$-MMP and/or the bubble point pressure of the native crude oil). Managing $CO_2$-MMP as disclosed herein provides a heretofore unknown and economical method of injecting $CO_2$ into a reservoir during tertiary oil recovery.

The herein presented method of lowering the $CO_2$-crude oil MMP in oil reservoirs so that $CO_2$ can be injected at a lower reservoir pressure is unexpected given the misconception in the oil industry that a reservoir must be pressurized to the $CO_2$-MMP of the original crude oil (or the bubble point pressure, when the bubble point pressure is higher than the $CO_2$-MMP in the original crude oil) prior to $CO_2$ injection for EOR.

EXAMPLES

The embodiments having been generally described, the following examples are given as particular embodiments of the disclosure and to demonstrate the practice and advantages thereof. It is understood that the examples are given by way of illustration and are not intended to limit the specification or the claims in any manner.

Figure 5:
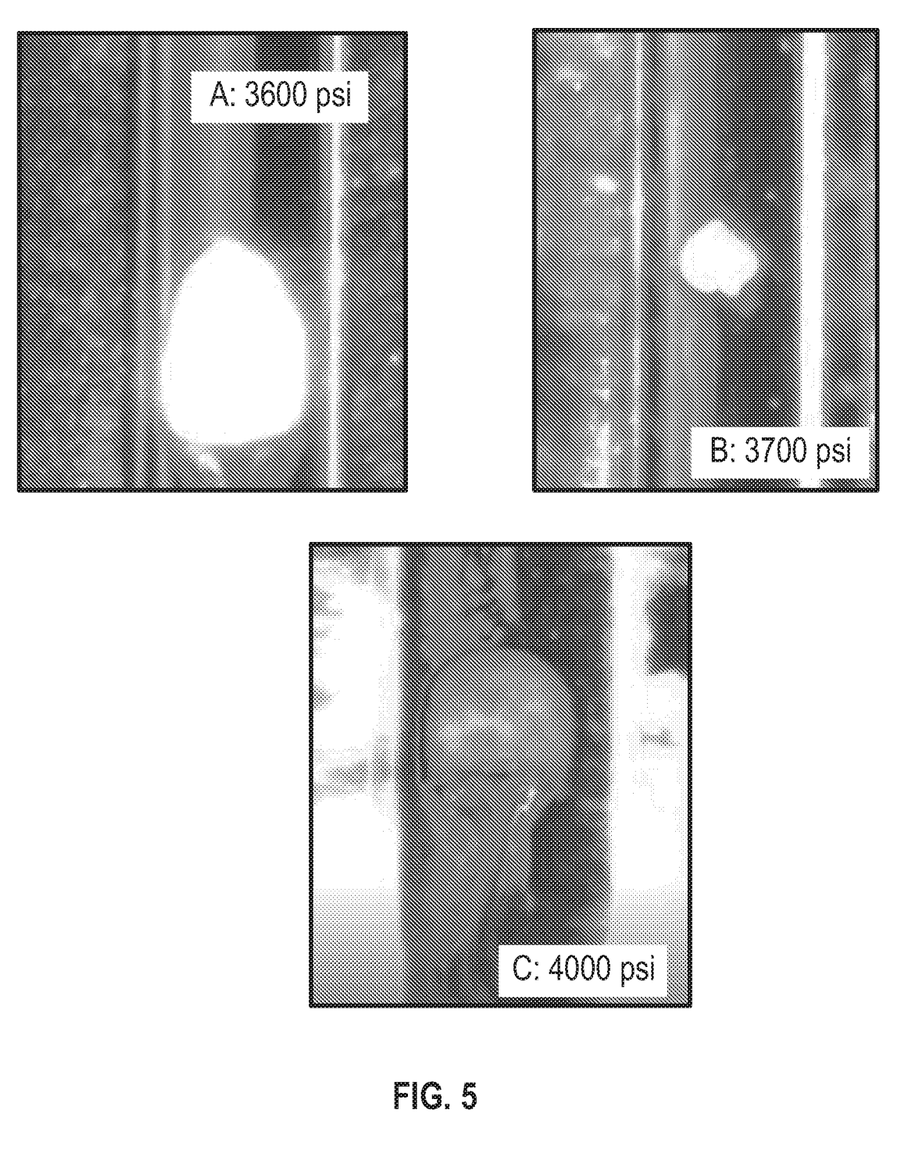
FIG. 5 shows results from the $CO_2$-crude oil Rising Bubble Apparatus (RBA) experiments of Example 1 at pressures of 3600 psi (Panel A), 3700 psi (Panel B), and 4000 psi (Panel C).
Figure 6:
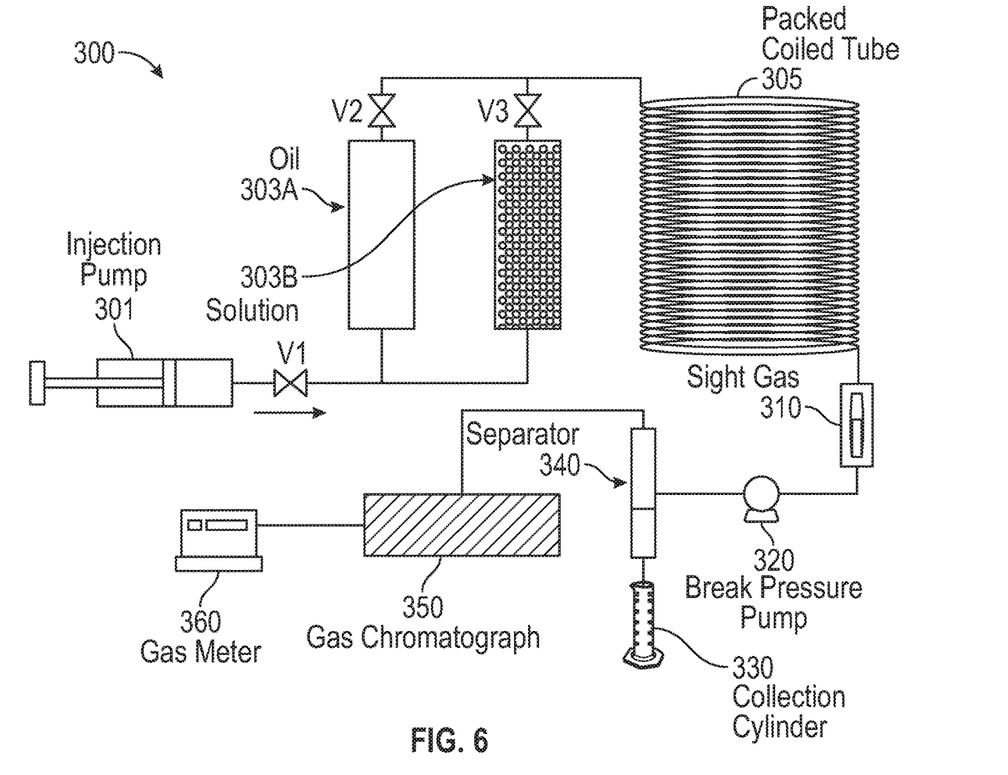
FIG. 6 is a schematic of a Slim-Tube apparatus utilized to determine the $CO_2$-MMP of crude oil in Example 1.
Figure 7:
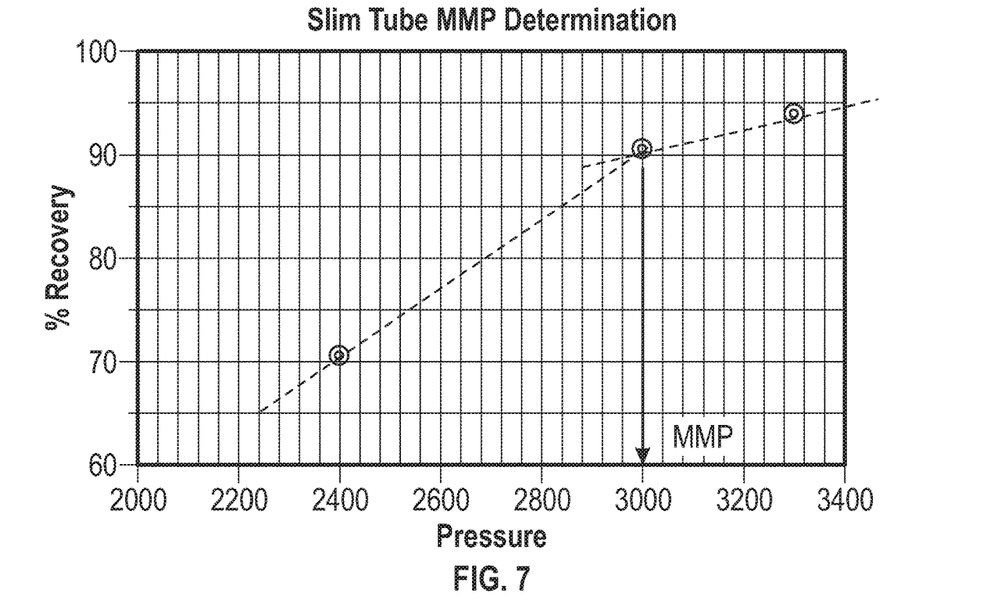
FIG. 7 is a plot of percent (%) recovery as a function of pressure utilized in the Slim-Tube $CO_2$-crude oil MMP determination of Example 1.

Example 1: Variation of Bubble Point Pressure and $CO_2$-MMP with Oil Composition Laboratory measurements were conducted with a live crude oil at different bubble point pressures from a reservoir in India to measure $CO_2$-MMP using the two widely accepted techniques of Rising Bubble Apparatus (RBA) method and Slim-Tube method. These two are well accepted MMP measurement methods used widely in the industry. The reservoir oil used in the rising bubble apparatus had a bubble point pressure of 3000 psi at 178° F. FIG. 5 shows results from the $CO_2$-crude oil RBA experiments at pressures of 3600 psi (Panel A), 3700 psi (Panel B), and 4000 psi (Panel C). As seen in Panel C of FIG. 5, at 4000 psi, the $CO_2$ bubble develops miscibility with the crude oil, indicating that the $CO_2$-MMP is about 4000 psi. The same crude oil was then pressure depleted to remove the lighter ends. This process reduced the bubble point pressure of the oil to 2000 psi. The light ends depleted oil was then used in a slim-tube apparatus to measure the $CO_2$-MMP. FIG. 6 is a schematic of the slim-tube apparatus 300 utilized for the $CO_2$-crude oil MMP determination. Slim-Tube Apparatus 300 comprised an injection pump 301 connected via a valve V1 to oil column 303A and solvent column 303B. The outputs of oil column 303A and solvent reservoir or column 303B were introduced into packed coiled tube 305 via valves V2 and V3, respectively. Sight glass 310 enabled visible observation of the output of packed coiled tube 305. Back pressure pump 320 was utilized to maintain a desired pressure throughout. Separator 340 was located downstream of back pressure pump 320. Separator 340 was connected with collection cylinder 330 and gas chromatograph 350. Gas chromatograph 350 was connected to a gas meter 360. FIG. 7 is a plot of the percent (%) recovery from the Slim-Tube experiments as a function of pressure utilized to determine the $CO_2$-MMP for the lights-depleted crude oil. The experimental results show that the $CO_2$-MMP of this light ends depleted oil was about 3000 psi. From these experiments, it is evident that depletion of light components (e.g., C1) from the crude oil resulted in a lower bubble point pressure and a lower $CO_2$-MMP.

The results of the experiments revealed that the reservoir oil with a higher mole fraction of light ends (bubble point pressure of 3000 psi) shows a high $CO_2$-MMP (about 4000 psi). The same reservoir oil, when depleted of the light ends, had a lower bubble point pressure (2000 psi) and a lower $CO_2$-MMP (3000 psi).

In summary, the results presented above indicate that lowering a mole fraction of light ends (e.g., C1) and increasing a mole fraction of intermediates (e.g., C2-C6) in a crude oil resulted in a lower $CO_2$-MMP. In this specific example, the original reservoir crude oil had a bubble point pressure of 3000 psi, and a $CO_2$-MMP for this saturated crude oil was about 4000 psi, while a pressure-depleted sample of the same crude oil (comprising a reduced amount of the lighter ends (e.g., C1)), had a bubble point pressure of 2000 psi, for which lab measurement for the crude oil at the new saturation conditions showed a $CO_2$-MMP of about 3000 psi. Thus, the $CO_2$-MMP fell from 4000 psi to 3000 psi (e.g., a reduction of 25%) by the pressure depletion of the original reservoir oil. If the reservoir pressure in the field has decreased to a value lower than 3000 psi, this oil reservoir pressure can be increased up to a depletion pressure of 3000 psi or a couple of hundred psi above this value, rather than, as conventionally believed necessary, back to the original $CO_2$-MMP of the native crude oil (e.g., 4000 psi). The method of this disclosure utilizes this discovery to recommend an optimal pressure depletion strategy during $CO_2$ EOR. Accordingly, the method of this disclosure facilitates gas injection EOR.

While various exemplary embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$ and an upper limit, $R_U$ is disclosed, any number falling within the range is specifically disclosed. In particular, the following numbers within the range are specifically disclosed: $R=R_L+k^*(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

Additional Disclosure

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method of recovering crude oil from a reservoir, the method comprising: determining a depletion pressure for providing a lights-depleted crude oil comprising a reduced amount of light ends including methane, nitrogen, carbon dioxide ($CO_2$), or a combination thereof and having a $CO_2$ multi contact Minimum Miscibility Pressure ($CO_2$-MMP) below a $CO_2$-MMP of a native crude oil, wherein the native crude oil is crude oil extracted from the reservoir prior to primary oil recovery therefrom; depleting the pressure of the reservoir from an initial reservoir pressure to the determined depletion pressure, thus providing the lights-depleted crude oil; repressurizing the reservoir to an operating pressure for recovering the lights-depleted crude oil from the reservoir via carbon dioxide ($CO_2$) injection; injecting $CO_2$ into the reservoir via at least one injection well; and recovering at least a portion of the lights-depleted crude oil from the reservoir via at least one production well.

B: A method of recovering crude oil from a reservoir via carbon dioxide ($CO_2$) injection, the method comprising: determining a depletion pressure by: (i) determining a $CO_2$ multi contact Minimum Miscibility Pressure ($CO_2$-MMP) for a sample having a composition of a native crude oil, wherein the native crude oil is crude oil extracted from the reservoir prior to primary oil recovery therefrom; (ii) pressure depleting a sample having a composition of the native crude oil to a test pressure; (iii) removing excess gas from the pressure depleted sample to provide a lights-depleted crude oil sample; (iv) measuring the $CO_2$-MMP for the lights-depleted crude oil sample at the test pressure; (v) repeating (ii) through (iv) for a plurality of test pressures; and (vi) determining the depletion pressure as the test pressure at which a lowest $CO_2$-MMP is obtained, depleting a pressure in the reservoir from an initial reservoir pressure to a pressure greater than or equal to the depletion pressure, whereby light components are removed from the reservoir to provide a lights-depleted crude oil in the reservoir, wherein light components comprise methane ($CH_4$), nitrogen ($N_2$), $CO_2$, or a combination thereof; and producing at least a portion of the lights-depleted crude oil from the reservoir via $CO_2$ injection at a reservoir pressure (or 'operating pressure') of greater than or equal to the $CO_2$-MMP of the lights-depleted crude oil.

C: a method of recovering crude oil from a reservoir via carbon dioxide ($CO_2$) injection, the method comprising: injecting $CO_2$ into the reservoir at an operating pressure of less than a $CO_2$ multi contact Minimum Miscibility Pressure ($CO_2$-MMP) of a native crude oil, wherein the native crude oil is crude oil extracted from the reservoir prior to primary oil recovery therefrom.

D: A method of recovering crude oil from a reservoir via carbon dioxide ($CO_2$) injection, the method comprising: depleting a pressure in the reservoir from an initial reservoir pressure, whereby light components are removed from the reservoir to provide a lights-depleted crude oil in the reservoir, wherein light components comprise methane ($CH_4$), nitrogen ($N_2$), $CO_2$, or a combination thereof; and producing at least a portion of the lights-depleted crude oil from the reservoir via $CO_2$ injection at an operating pressure of greater than or equal to the $CO_2$-MMP of the lights-depleted crude oil and less than the $CO_2$-MMP of a native crude oil, wherein the native crude oil is crude oil extracted from the reservoir prior to primary recovery therefrom.

Each of embodiments A, B, C, and D may have one or more of the following additional elements: Element 1: wherein the depletion pressure is a pressure below which the $CO_2$ multi contact Minimum Miscibility Pressure ($CO_2$-MMP) does not further decrease during $CO_2$-MMP experiments on the native crude oil. Element 2: wherein the operating pressure is less than the $CO_2$-MMP for the native crude oil. Element 3: wherein the operating pressure is in a range of from about 5-35%, 15-35%, 15-50% less than the $CO_2$-MMP for the native crude oil, or at least 5, 10, 15, 20, 25, 30, or 35% less than the $CO_2$-MMP for the native crude oil. Element 4: wherein the operating pressure is below the bubble point pressure of the native crude oil, wherein the bubble point pressure is the pressure at which a first bubble of gas is liberated from the liquid phase at the reservoir temperature. Element 5: wherein a bubble point pressure of the lights-depleted crude oil is in a range of from about 5-50%, 25-45%, or 20-60% less than the bubble point pressure of the native crude oil, or greater than or equal to 5, 10, 15, 20, 25, 30, 35, 40, or 45% less than the bubble point pressure of the native crude oil. Element 6: wherein determining the depletion pressure comprises: (i) determining the $CO_2$-MMP for a sample having a composition of the native crude oil; (ii) pressure depleting a sample having a composition of the native crude oil to a test pressure; (iii) removing excess gas from the pressure depleted sample to provide a lights-depleted crude oil sample; (iv) measuring the $CO_2$-MMP for the lights-depleted crude oil sample at the test pressure; (v) repeating (ii) through (iv) for a plurality of test pressures; and (vi) utilizing the $CO_2$-MMP values for the lights-depleted crude oil samples produced at the corresponding test pressures to determine the depletion pressure. Element 7: wherein (vi) further comprises determining the depletion pressure as the test pressure at which the $CO_2$-MMP for the lights-depleted crude oil sample is a minimum. Element 8: wherein determining the depletion pressure as the test pressure at which the $CO_2$-MMP for the lights-depleted crude oil sample is a minimum further comprises plotting the $CO_2$-MMP as a function of the test pressure for each of the samples. Element 9: wherein the lights-depleted crude oil comprises a mole fraction of light ends that is in a range of from about 5-50%, 10-30%, or 10-50% less than a mole fraction of light ends in the native crude oil, or at least 5, 10, 15, 20, 25, or 30% less than a mole fraction of light ends in the native crude oil, wherein the light ends comprise methane ($CH_4$), nitrogen ($N_2$), $CO_2$, or a combination thereof. Element 10: wherein the lights-depleted crude oil comprises a mole fraction of intermediate components that is in a range of from about 5-50%, 10-30%, or 10-50% greater than a mole fraction of intermediate components in the native crude oil, or at least 5, 10, 15, 20, 25, or 30% greater than a mole fraction of intermediate components in the native crude oil, wherein the intermediate components have molecular weights (MWs) between that of ethane (C2) and hexane (C6). Element 11: wherein the producing is effected at an operating pressure less than the $CO_2$-MMP for the native crude oil. Element 12: wherein producing is effected at an operating that is in a range of from 10-35%, 15-35%, or 10-50% less than the $CO_2$-MMP for the native crude oil, or at least 15, 20, 25, 30, or 35% less than the $CO_2$-MMP for the native crude oil. Element 13: wherein the producing is effected at an operating pressure less than a bubble point pressure of the native crude oil, wherein the bubble point pressure is the pressure at which a first bubble of gas is liberated from the liquid phase at the reservoir temperature. Element 14: wherein a bubble point pressure of the lights-depleted crude oil is in a range of from 20-50, 25-35%, or 20-35% less than the bubble point pressure of the native crude oil, or at least 25, 30, or 35% less than the bubble point pressure of the native crude oil. Element 15: wherein the bubble point pressure of the native crude oil is greater than or equal to the $CO_2$-MMP of the native crude oil. Element 16: wherein the $CO_2$-MMP of the native crude oil is greater than the initial reservoir pressure. Element 17: wherein the operating pressure is in a range of from 25-50%, 30-40%, or 25-40% less than the $CO_2$-MMP for the native crude oil, or is at least 30, 35, or 40% less than the $CO_2$-MMP for the native crude oil. Element 18: wherein the operating pressure is below the bubble point pressure of the native crude oil, wherein the bubble point pressure is the pressure at which a first bubble of gas is liberated from the liquid phase at the reservoir temperature. Element 19: wherein the operating pressure is in a range of from 10-30%, 15-25%, or 20-30% less than the bubble point pressure of the native crude oil, or is at least 15, 20, or 25% less than the bubble point pressure of the native crude oil. Element 20: further comprising depleting the reservoir of light ends to provide a lights-depleted crude oil in the reservoir prior to injecting the $CO_2$ into the reservoir, wherein the light ends comprise methane ($CH_4$), nitrogen ($N_2$), $CO_2$, or a combination thereof. Element 21: wherein depleting the reservoir of the light ends increases a mole fraction of intermediate components in the lights-depleted crude oil by at least 10-30% and decreases a mole fraction of light ends in the lights-depleted crude oil by at least 10-30%, wherein the light ends comprise methane ($CH_4$), nitrogen ($N_2$), $CO_2$, or a combination thereof, and wherein the intermediate components include components having a molecular weights (MW) between that of ethane (C2) and hexane (C6).

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference. Unless expressly stated otherwise, the steps in a method claim may be performed in any order and with any suitable combination of materials and processing conditions.

The invention claimed is:

1. A method of recovering crude oil from a reservoir, the method comprising:
    determining a depletion pressure for providing a lights-depleted crude oil comprising a reduced amount of light ends including methane, nitrogen, carbon dioxide ($CO_2$), or a combination thereof and having a $CO_2$ multi contact Minimum Miscibility Pressure ($CO_2$-MMP) below a $CO_2$-MMP of a native crude oil, wherein the native crude oil is crude oil extracted from the reservoir prior to primary oil recovery therefrom;
    depleting the pressure of the reservoir from an initial reservoir pressure to the determined depletion pressure, thus providing the lights-depleted crude oil;
    repressurizing the reservoir to an operating pressure for recovering the lights-depleted crude oil from the reservoir via carbon dioxide ($CO_2$) injection;
    injecting $CO_2$ into the reservoir via at least one injection well; and
    recovering at least a portion of the lights-depleted crude oil from the reservoir via at least one production well.

2. The method of claim 1, wherein the depletion pressure is a pressure below which the $CO_2$ multi contact Minimum Miscibility Pressure ($CO_2$-MMP) does not further decrease during $CO_2$-MMP experiments on the native crude oil.

3. The method of claim 1, wherein the operating pressure is less than the $CO_2$-MMP for the native crude oil.

4. The method of claim 3, wherein the operating pressure is 15-35% less than the $CO_2$-MMP for the native crude oil.

5. The method of claim 3, wherein the operating pressure is below the bubble point pressure of the native crude oil, wherein the bubble point pressure is the pressure at which a first bubble of gas is liberated from the liquid phase at the reservoir temperature.

6. The method of claim 5, wherein a bubble point pressure of the lights-depleted crude oil is 25-45% less than the bubble point pressure of the native crude oil.

7. The method of claim 1, wherein determining the depletion pressure comprises:
    (i) determining the $CO_2$-MMP for a sample having a composition of the native crude oil;
    (ii) pressure depleting a sample having a composition of the native crude oil to a test pressure;
    (iii) removing excess gas from the pressure depleted sample to provide a lights-depleted crude oil sample;
    (iv) measuring the $CO_2$-MMP for the lights-depleted crude oil sample at the test pressure;
    (v) repeating (ii) through (iv) for a plurality of test pressures; and
    (vi) utilizing the $CO_2$-MMP values for the lights-depleted crude oil samples produced at the corresponding test pressures to determine the depletion pressure.

8. The method of claim 7, wherein (vi) further comprises determining the depletion pressure as the test pressure at which the $CO_2$-MMP for the lights-depleted crude oil sample is a minimum.

9. The method of claim 8, wherein determining the depletion pressure as the test pressure at which the $CO_2$-MMP for the lights-depleted crude oil sample is a minimum further comprises plotting the $CO_2$-MMP as a function of the test pressure for each of the samples.

10. The method of claim 1, wherein the lights-depleted crude oil comprises a mole fraction of light ends that is 10-30% less than a mole fraction of light ends in the native crude oil.

11. The method of claim 1, wherein the lights-depleted crude oil comprises a mole fraction of intermediate components that is 10-30% greater than a mole fraction of intermediate components in the native crude oil, wherein the intermediate components have molecular weights (MWs) between that of ethane (C2) and hexane (C6).

12. A method of recovering crude oil from a reservoir via carbon dioxide ($CO_2$) injection, the method comprising:
   determining a depletion pressure by:
      (i) determining a $CO_2$ multi contact Minimum Miscibility Pressure ($CO_2$-MMP) for a sample having a composition of a native crude oil, wherein the native crude oil is crude oil extracted from the reservoir prior to primary oil recovery therefrom;
      (ii) pressure depleting a sample having a composition of the native crude oil to a test pressure;
      (iii) removing excess gas from the pressure depleted sample to provide a lights-depleted crude oil sample;
      (iv) measuring the $CO_2$-MMP for the lights-depleted crude oil sample at the test pressure;
      (v) repeating (ii) through (iv) for a plurality of test pressures; and
      (vi) determining the depletion pressure as the test pressure at which a lowest $CO_2$-MMP is obtained,
   depleting a pressure in the reservoir from an initial reservoir pressure to a pressure greater than or equal to the depletion pressure, whereby light components are removed from the reservoir to provide a lights-depleted crude oil in the reservoir, wherein light components comprise methane ($CH_4$), nitrogen ($N_2$), $CO_2$, or a combination thereof; and
   producing at least a portion of the lights-depleted crude oil from the reservoir via $CO_2$ injection at an operating pressure of greater than or equal to the $CO_2$-MMP of the lights-depleted crude oil.

13. The method of claim 12, wherein the producing is effected at an operating pressure less than the $CO_2$-MMP for the native crude oil.

14. The method of claim 13, wherein the producing is effected at an operating pressure that is 15-35% less than the $CO_2$-MMP for the native crude oil.

15. The method of claim 12, wherein the producing is effected at a pressure less than a bubble point pressure of the native crude oil, wherein the bubble point pressure is the pressure at which a first bubble of gas is liberated from the liquid phase at the reservoir temperature.

16. The method of claim 12, wherein a bubble point pressure of the lights-depleted crude oil is 25-35% less than the bubble point pressure of the native crude oil.

17. The method of claim 12, wherein the bubble point pressure of the native crude oil is greater than or equal to the $CO_2$-MMP of the native crude oil.

18. The method of claim 12, wherein the $CO_2$-MMP of the native crude oil is greater than the initial reservoir pressure.

19. A method of recovering crude oil from a reservoir via carbon dioxide ($CO_2$) injection, the method comprising:
   injecting $CO_2$ into the reservoir at an operating pressure of less than a $CO_2$ multi contact Minimum Miscibility Pressure ($CO_2$-MMP) of a native crude oil, wherein the native crude oil is crude oil extracted from the reservoir prior to primary oil recovery therefrom; and
   depleting the reservoir of light ends to provide a lights-depleted crude oil in the reservoir prior to injecting the $CO_2$ into the reservoir, wherein the light ends comprise methane ($CH_4$), nitrogen ($N_2$), $CO_2$, or a combination thereof.

20. The method of claim 19, wherein depleting the reservoir of the light ends increases a mole fraction of intermediate components in the lights-depleted crude oil by 10-30% and decreases a mole fraction of light ends in the lights-depleted crude oil by 10-30%, wherein the light ends comprise methane ($CH_4$), nitrogen ($N_2$), $CO_2$ or a combination thereof, and wherein the intermediate components include components having a molecular weights (MW) between that of ethane (C2) and hexane (C6).

21. The method of claim 19, wherein the operating pressure is 30-40% less than the $CO_2$-MMP for the native crude oil.

22. The method of claim 19, wherein the operating pressure is below the bubble point pressure of the native crude oil, wherein the bubble point pressure is the pressure at which a first bubble of gas is liberated from the liquid phase at the reservoir temperature.

23. The method of claim 22, wherein the operating pressure is 15-25% less than the bubble point pressure of the native crude oil.

* * * * *